US00PP25248P2

(12) United States Plant Patent
Klein

(10) Patent No.: US PP25,248 P2
(45) Date of Patent: Jan. 27, 2015

(54) ***VERONICA* PLANT NAMED 'MARIETTA'**

(50) Latin Name: *Veronica longifolia*
Varietal Denomination: Marietta

(71) Applicant: Ruud Klein, Roelofarendsveen (NL)

(72) Inventor: Ruud Klein, Roelofarendsveen (NL)

(73) Assignee: Rijnbeek and Son Perennial Export B.V., Boskoop (NL)

( * ) Notice: Subject to any disclaimer, the term of this patent is extended or adjusted under 35 U.S.C. 154(b) by 12 days.

(21) Appl. No.: 13/986,654

(22) Filed: May 21, 2013

(51) Int. Cl.
*A01H 5/00* (2006.01)

(52) U.S. Cl.
USPC ..... Plt./251

(58) Field of Classification Search
USPC ..... Plt./251
See application file for complete search history.

*Primary Examiner* — Kent L Bell
(74) *Attorney, Agent, or Firm* — C. A. Whealy

(57) ABSTRACT

A new and distinct cultivar of *Veronica* plant named 'Marietta', characterized by its upright plant habit with strong stems; dark green-colored leaves; early flowering response; dense inflorescences with numerous dark violet-colored flowers; and good garden performance.

3 Drawing Sheets

Botanical designation: *Veronica longifolia.*
Cultivar denomination: 'MARIETTA'.

BACKGROUND OF THE INVENTION

The present invention relates to a new and distinct cultivar of *Veronica* plant, botanically known as *Veronica longifolia* and hereinafter referred to by the name 'Marietta'.

The new *Veronica* plant is a naturally-occurring branch mutation of *Veronica longifolia* 'Allmelanie', not patented. The new *Veronica* plant was discovered and selected by the Inventor on a single flowering plant from within a population of plants of 'Allmelanie' in a controlled outdoor nursery environment in Roelofarendsveen, The Netherlands on Jul. 1, 2008.

Asexual reproduction of the new *Veronica* plant by softwood cuttings in a controlled environment in Roelofarendsveen, The Netherlands since Oct. 1, 2008, has shown that the unique features of this new *Veronica* plant are stable and reproduced true to type in successive generations.

SUMMARY OF THE INVENTION

Plants of the new *Veronica* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Marietta'. These characteristics in combination distinguish 'Marietta' as a new and distinct *Veronica* plant:

1. Upright plant habit with strong stems.
2. Dark green-colored leaves.
3. Early flowering response.
4. Dense inflorescences with numerous dark violet-colored flowers.
5. Good garden performance.

Plants of the new *Veronica* differ primarily from plants of the parent, 'Allmelanie', in the following characteristics:

1. Plants of the new *Veronica* have stronger stems than plants of 'Allmelanie'.
2. Plants of the new *Veronica* have darker green-colored leaves than plants of 'Allmelanie'.
3. Plants of the new *Veronica* flower about four weeks earlier than plants of 'Allmelanie'.
4. Plants of the new *Veronica* have darker violet-colored flowers than plants of 'Allmelanie'.

Plants of the new *Veronica* can be compared to plants of *Veronica longifolia* 'Charlotte', disclosed in U.S. Plant Pat. No. 23,803. In side-by-side comparisons conducted in Roelofarendsveen, The Netherlands, plants of the new *Veronica* differed primarily from plants of 'Charlotte' in leaf and flower color as plants of 'Charlotte' had variegated leaves and white-colored flowers.

BRIEF DESCRIPTION OF THE PHOTOGRAPHS

The accompanying colored photographs illustrate the overall appearance of the *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet comprises a side perspective view of a typical flowering plant of 'Marietta' grown in a container.

The photograph on the second sheet is a close-up view of a typical leaf of 'Marietta'.

The photograph on the third sheet is a close-up view of a typical flowering plant of 'Marietta'.

DETAILED BOTANICAL DESCRIPTION

Plants used for the aforementioned photographs and following description were grown during the autumn in an outdoor nursery in Woubrugge, The Netherlands and under cultural practices which closely approximate commercial *Veronica* production. During the production of the plants, day temperatures ranged from 10° C. to 23° C. and night temperatures ranged from 1° C. to 14° C. Plants were two years old when the photographs and the description were taken. In the following description, color references are made to The Royal Horticultural Society Colour Chart, 2007 Edition, except where general terms of ordinary dictionary significance are used.

Botanical classification: *Veronica longifolia* 'Marietta'.

Parentage: Naturally-occurring branch mutation of *Veronica longifolia* 'Allmelanie', not patented.

Propagation:

*Type cutting*.—Softwood cuttings.

*Time to initiate roots, summer*.—About ten days at 20° C.

*Time to produce a rooted young plant, summer*.—About 13 weeks at 20° C.

*Root description*.—Medium in thickness, fibrous; light brown to whitish brown in color.

*Rooting habit*.—Moderately freely branching; medium density.

Plant description:

*Plant type*.—Herbaceous perennial.

*Plant and growth habit*.—Upright, roughly oblong in shape; basal branching habit with about 14 main stems, pinching enhances branch development; moderately vigorous growth habit.

*Plant height*.—About 38.5 cm.

*Plant width*.—About 33.8 cm.

*Lateral branch description*.—Length: About 24.8 cm. Diameter: About 3 mm. Internode length: About 4.1 cm. Strength: Strong. Texture: Densely pubescent. Color: Close to between 138A and 143A.

Leaf description:

*Arrangement*.—Opposite, simple.

*Length*.—About 7.2 cm.

*Width*.—About 3.4 cm.

*Shape*.—Narrowly ovate.

*Apex*.—Acute.

*Base*.—Truncate to short attenuate.

*Margin*.—Serrate.

*Texture, upper and lower surfaces*.—Sparsely to moderately pubescent.

*Venation pattern*.—Pinnate.

*Color*.—Developing leaves, upper surface: Darker than between N137A and 143A. Developing leaves, lower surface: Between 143A and 146A. Fully expanded leaves, upper surface: Close to N137A; venation, close to 145B. Fully expanded leaves, lower surface: Close to between 138A and 147B; venation, close to 144B.

*Petiole length*.—About 1.5 cm.

*Petiole diameter*.—About 2 mm.

*Petiole texture, upper and lower surfaces*.—Sparsely pubescent.

*Petiole color, upper and lower surfaces*.—Close to 144B.

Flower description:

*Flower shape and arrangement*.—Single campanulate flowers arranged on dense compound terminal racemes; flowers face mostly outwardly.

*Flowering habit*.—Freely flowering, about 300 flowers develop per raceme.

*Fragrance*.—Faintly fragrant.

*Natural flowering season*.—Plants begin flowering about 20 weeks after deadheading; flowering in the garden from early July to mid-October in The Netherlands.

*Flower longevity on the plant*.—About one week; flowers not persistent.

*Flower buds*.—Length: About 5 mm. Diameter: About 2 mm. Shape: Narrowly ovate to oblong. Color: Close to N89A.

*Inflorescence height*.—About 13.3 cm.

*Inflorescence diameter*.—About 2.6 cm.

*Flower diameter*.—About 7 mm.

*Flower height*.—About 1 cm.

*Petals*.—Quantity and arrangement: About four in a single whorl, petals fused about 45% of the length from the base. Length: About 7 mm. Width: About 4 mm. Shape: Oblanceolate. Apex: Broadly acute. Margin: Entire. Texture, upper and lower surfaces: Smooth, glabrous. Color: When opening and fully opened, upper surface: Close to N88A; color becoming closer to N92B with development. When opening and fully opened, lower surface: Close to N88A.

*Sepals*.—Quantity and arrangement: About four in a single whorl, sepals fused about 5% of the length from the base. Length: About 2.5 mm. Width: About 1 mm. Shape: Narrowly ovate. Apex: Acute. Margin: Entire. Texture, upper and lower surfaces: Smooth, glabrous. Color: When opening and fully opened, upper surface: Close to 137D. When opening and fully opened, lower surface: Close to 137D.

*Peduncles*.—Length: About 12.7 cm. Diameter: About 2 mm. Aspect: Primary racemes, mostly upright; secondary racemes, about 25° from vertical. Strength: Strong. Texture: Smooth, glabrous. Color: Close to 143A to 143B.

*Pedicels*.—Length: About 1.5 mm. Diameter: About 0.5 mm. Aspect: About 65° from vertical. Strength: Strong. Texture: Smooth, glabrous. Color: Close to 143B.

*Reproductive organs*.—Stamens: Quantity per flower: Two. Filament length: About 9 mm. Filament color: Close to 90A to 90B. Anther length: About 1 mm. Anther shape: Elliptical. Anther color: Close to 86B. Pollen amount: Abundant. Color: Close to 4D. Pistils: Quantity per flower: One. Pistil length: About 8 mm. Stigma shape: Clavate. Stigma color: Close to N92B. Style length: About 7.5 mm. Style color: Close to 90A to 90B. Ovary color: Close to 144B.

*Seeds and fruits*.—Seed and fruit development have not been observed on plants of the new *Veronica*.

Disease & pest resistance: Plants of the new *Veronica* have not been noted to be resistant to pathogens and pests common to *Veronica*.

Garden performance: Plants of the new *Veronica* have exhibited good garden performance and to tolerate rain, wind, high temperatures of about 35° C. and to be hardy to USDA Hardiness Zone 4.

It is claimed:

1. A new and distinct *Veronica* plant named 'Marietta' as illustrated and described.

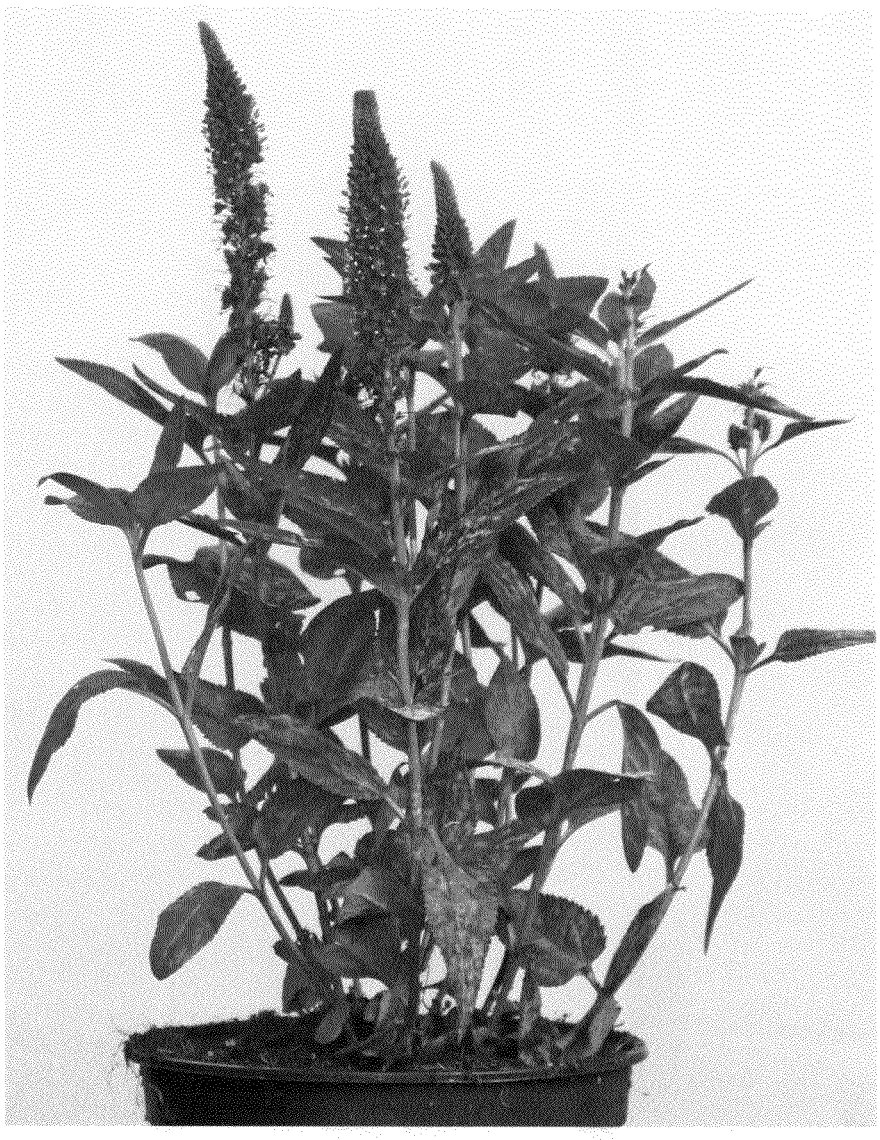

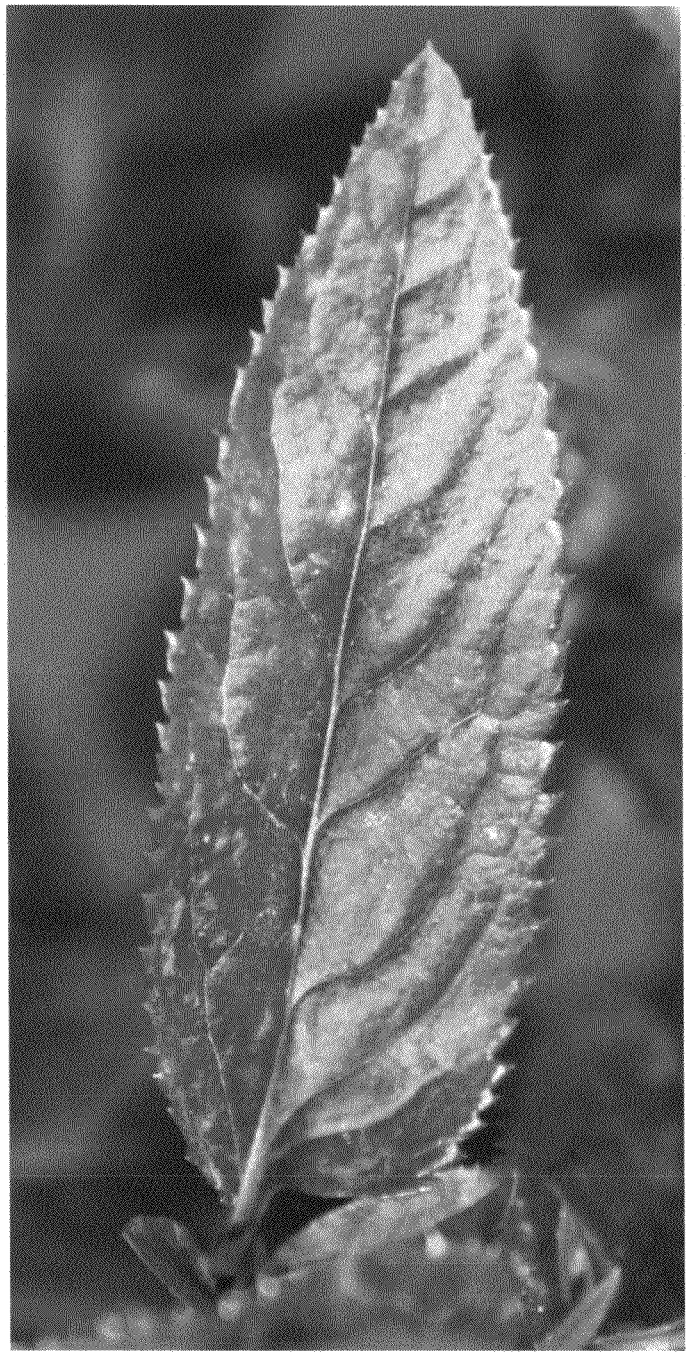

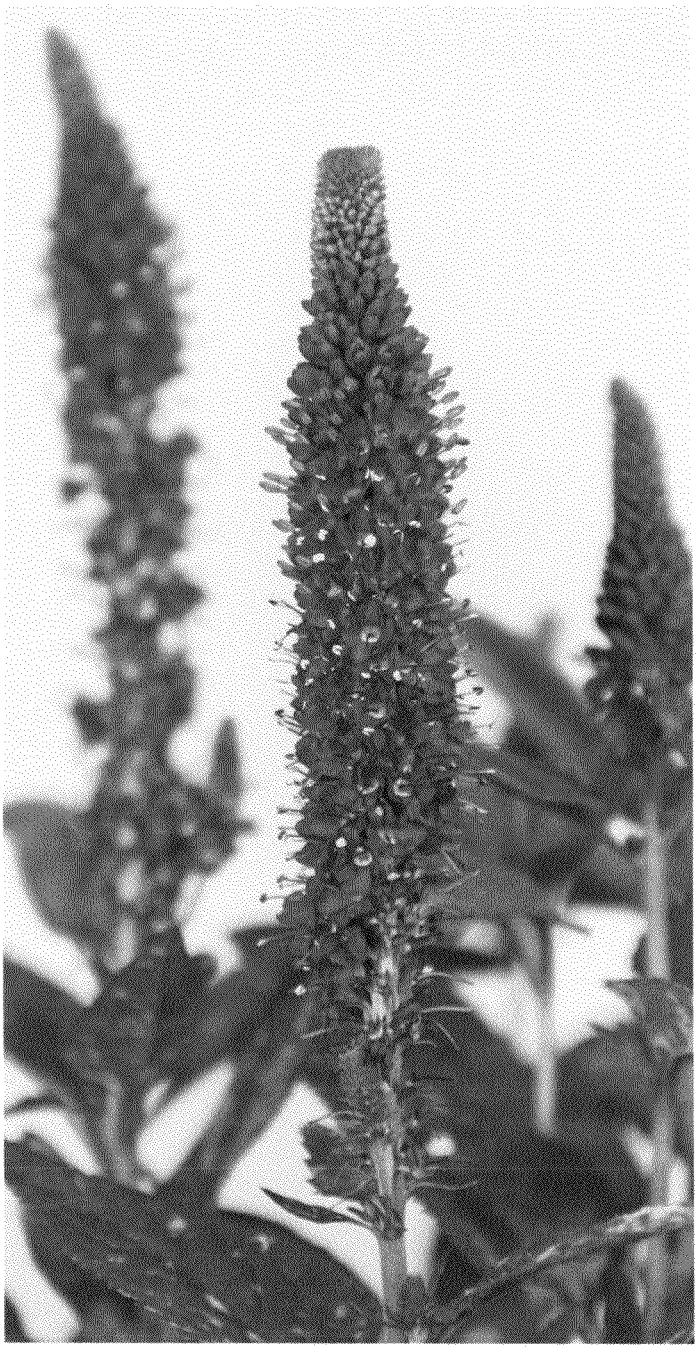

* * * * *